United States Patent [19]

Batalin et al.

[11] 4,246,247

[45] Jan. 20, 1981

[54] METHOD OF PREPARING A CALCIUM PHOSPHATE CATALYST

[76] Inventors: Oleg E. Batalin, ulitsa Ordzhonikidze, 45, kv. 85; Arkady S. Dykman, ulitsa Leni Golikova, 37, korpus, 4, kv. 15, both of Leningrad; Izrail M. Belgorodsky, Molodezhny bulvar, 50, kv. 25, Tolyatti; Oleg A. Ostroukhov, ulitsa Karla Marxa, 52, kv. 31, Tolyatti; Ljudmila V. Golovko, ulitsa Matrosova, 30, kv. 180, Tolyatti; Vladimir I. Nevstruev, ulitsa Karla Marxa, 52, kv. 31, Tolyatti; Anatoly I. Lukashov, ulitsa Palekhskaya, 9/1, kv. 65, Moscow, all of U.S.S.R.

[21] Appl. No.: 66,495

[22] Filed: Aug. 14, 1979

[51] Int. Cl.³ .............................................. B01J 11/82
[52] U.S. Cl. .................................. 423/311; 252/437; 423/308
[58] Field of Search ............... 423/309, 310, 311, 308; 252/437

[56] References Cited

U.S. PATENT DOCUMENTS 3,846,338  11/1974  Kachlova et al. ................... 252/437

*Primary Examiner*—O. H. Veritz
*Assistant Examiner*—Wayne A. Langel
*Attorney, Agent, or Firm*—Fleit & Jacobson

[57] ABSTRACT

Disclosed is a method of preparing a calcium phosphate catalyst, which comprises reacting a calcium salt with a phosphoric acid salt in aqueous ammonia, separating the precipitate resulting from the reaction mixture thus obtained, suitably shaping said precipitate, drying it, and subjecting it to heat treatment within a temperature range of 450° to 600° C. in the presence of steam mixed with at least one of the components selected from the group consisting of an inert gas, air, phosphoric an acid, aldehyde, an oxygen-containing heterocyclic compound, an alcohol, and a diene hydrocarbon.

The reaction of calcium salts with phosphoric acid salts in aqueous ammonia is effected with the starting reactants taken in the molar ratio of 1.5:1 if no phosphoric acid treatment is used, or with the starting reactants in a molar ratio within the range of 1.5:1 to 5.0:1 if the reaction mixture is treated with a phosphoric acid solution to a pH of from 5.0 to 7.0.

11 Claims, No Drawings

METHOD OF PREPARING A CALCIUM PHOSPHATE CATALYST

FIELD OF THE INVENTION

The present invention relates to the production of catalysts such as can be used, for example, in the manufacture of isoprene from isobutylene and formaldehyde, and more particularly to a method of preparing a calcium phosphate catalyst for use in decomposing 1,3-dioxanes and, in particular, 4,4-dimethyl-1,3-dioxane (hereinafter referred to as DMD) into isoprene, as well as in alcohol dehydration reactions.

BACKGROUND OF THE INVENTION

It has been known in the prior art to prepare phosphates of metals of Group II of the Periodic Table, usable as catalysts for selective cleavage of $\equiv$C—O— bonds in organic compounds, and, specifically, for converting 4,4-dimethyl-1,3-dioxane into isoprene, as well as for dehydration of alcohols, by precipitating normal phosphates of Group II metals from aqueous solutions of their salts taken in conjunction with water-soluble salts of phosphoric acid, followed by separating the precipitate, washing the paste obtained, and shaping it into catalyst granules (cf. U.S. Pat. No. 3,872,216).

Catalysts prepared by the above technique, however, are characterized by low selectivity (78–82 mole %), low activity resulting in low DMD space velocity (0.7 $h^{-1}$), and high operating temperatures (ca. 375° C.).

Selectivity is defined as the ratio of the amount in moles of isoprene formed to the amount in moles of DMD converted.

Selectivity is quantitatively dependent upon catalyst composition and structure, as well as upon the process conditions under which the catalyst operates.

Increased selectivity will lead to reduced stockfeed (DMD) consumption rates per unit of finished product, thus per ton of isoprene. The relatively low selectivity of the catalyst obtainable by the aforesaid prior technique would result in high feedstock consumption rates in isoprene production, varying between ca. 2.10 and 2.25 kg DMD per kg of isoprene.

The activity of calcium phosphate catalysts is dependent upon their acidity which is determined by the number and efficiency of the active centres and can be characterized by the DMD conversion degree.

DMD conversion is defined as the ratio of the amount of DMD converted to that of DMD used, expressed in percent.

There is also known in the art to produce calcium phosphate catalysts by reacting a calcium salt with a phosphoric acid salt in aqueous ammonia; followed by washing and drying the resulting precipitate and heat treatment with the use of super-heated steam or a mixture of steam and air at high temperatures (cf. U.S. Pat. No. 3,846,338).

The catalysts obtainable by this prior art technique are relatively low in activity.

Furthermore, calcium phosphate catalysts prepared by the aforesaid technique have a low efficiency (0.3 to 0.4 ton/h of isoprene per cubic meter of catalyst).

The efficiency of a catalyst depends on its activity and selectivity, as well as on the feedstock space velocity.

In the prior technique, heat treatment is carried out at high temperatures, which involves overheating of the heat carrier to temperatures as high as 650° to 800° C. and high process power inputs, as well as special heat-resistant materials for reactors adapted to produce the catalyst.

One further disadvantage associated with the catalyst obtainable by the aforesaid technique is a relatively short service life (250 hours).

The catalyst life depends on many factors including catalyst composition and structure, catalyst activity, operating temperatures, and coke deposition. Coke deposition is understood to denote coke deposits on the catalyst in the process of DMD decomposition. It is determinable as the ratio of the amount in moles of coke deposited to the amount in moles of DMD converted, expressed in percent.

In spite of the advantages inherent in the prior art technique for preparation of calcium phosphate catalysts, no commercial process based on said technique has been developed so far, since there is no catalyst as yet, with selectivity and stability such as to justify a commercial process.

SUMMARY OF THE INVENTION

It is an object of the present invention to provide a method for preparing a high-activity calcium phosphate catalyst.

Another object of this invention is to provide a method for preparing a high-efficiency calcium phosphate catalyst.

A further object of the present invention is to provide a method of preparing a high-selectivity calcium phosphate catalyst.

A still further object of the present invention is to provide a method of preparing a calcium phosphate catalyst, such as would enable the obtaining of catalysts with a long service life and low coke deposition during the service thereof.

With these and other objects in view, there is provided a method of preparing a calcium phosphate catalyst, which comprises reacting calcium salts with phosphoric acid salts in aqueous ammonia, separating the resulting precipitate from the reaction mixture, suitably shaping said precipitate, drying it, and subjecting it to heat treatment at high temperatures in the presence of steam, wherein, according to the invention, heat treatment is performed within a temperature range of 450° to 600° C. in the presence of steam mixed with phosphoric acid or an aldehyde, or an oxygen-containing heterocyclic compound, or an alcohol, or a diene hydrocarbon, or steam mixed with an inert gas or air and phosphoric acid, or steam mixed with an inert gas and an aldehyde, or an oxygen-containing heterocyclic compound, or an alcohol, or a diene hydrocarbon.

Formaldehyde and acetaldehyde are preferable to be used as said aldehyde.

It is advisable that as said oxygen-containing heterocyclic compound use is made of methyl dihydropyrane or methylene tetrahydropyrane.

The suitable alcohols are trimethyl carbinol and isopropenyl ethyl carbinol.

The suitable diene hydrocarbons are isoprene or piperylene.

It is also advisable that the reaction of calcium salts with phosphoric acid salts in an aqueous ammonia be carried out with the starting reactants taken in the molar ratio of 1.5:1.

The preferred embodiment is for the reaction of calcium salts with phosphoric acid salts in aqueous ammonia to be effected with the starting reactants taken in a molar ratio within 1.5:1 to 5.0:1 and for the reaction mixture obtained to be treated with a phosphoric acid solution to a pH of from 5.0 to 7.0.

It is desirable to treat the reaction mixture with a phosphoric acid solution to a pH of from 5.5 to 6.0.

According to the herein-proposed method, a catalyst can be obtained featuring high selectivity (86.0 to 87.5 mole %), high activity (96.0–97.0%), and low coke deposition (below 1 mole %).

The aforesaid and other objects and features of the present invention are set forth in the appended claims, and the present invention will be more fully apparent from the detailed description of its embodiments presented hereinunder.

DETAILED DESCRIPTION OF THE EMBODIMENTS

The proposed method of preparing a calcium phosphate catalyst can be realized as follows.

The starting reactants to be used are solutions of calcium salts, e.g. calcium chloride, and phosphoric acid salts, e.g. diammonium phosphate, disodium phosphate, etc. A suitable amount of agua ammonia is added to the phosphoric acid salt solution prior to reacting it with the calcium salt solution for pH control of the medium.

The calcium salt and phosphoric acid salt solutions are gradually introduced into a vessel fitted with a stirrer, while continuously stirring the slurry being formed. The reaction is carried out with the calcium salt and phosphoric acid salt taken in the molar ratio of 1.5:1. However, the reaction is realizable with the starting reactants having a molar ratio anywhere within the range of 1.5:1 to 5.0:1, preferably 2.5:1. In cases such as these, the reaction mixture is to be treated with a phosphoric acid solution to a pH of from 5.0 to 7.0, preferably 5.5 to 6.0.

The above ranges of molar ratios of calcium salts to phosphoric acid salts and pH values of the reaction medium are consistent with obtaining a calcium phosphate catalyst of desired structure and composition.

The resulting precipitate is separated by filtration or any other known method, washed with distilled water to remove calcium salt anions, shaped into granules by a conventional technique, and dried at a temperature between 110° and 140° C., thus obtaining a raw calcium phosphate which is then loaded for further treatment into a reactor.

The reactor is a quartz tube measuring 20 to 26 mm in diameter. The reactor is placed into an electrically heated oven for the catalyst enclosed in the reactor to be subjected to heat treatment at a temperature within 450° to 600° C., using steam with an addition of phosphoric acid or an organic compound.

The organic compounds that may be used as additions to steam include formaldehyde, acetaldehyde, methyl dihydropyrane (MDHP), methylene tetrahydropyrane (MTHP), trimethyl carbinol (TMC), isopropenyl ethyl carbinol (IPEA), isoprene, and piperylene.

Where a calcium phosphate catalyst is obtained without pretreatment of the reaction mixture with phosphoric acid solution, heat treatment is preferably performed at 450° C.

However, where the method of calcium phosphate catalyst preparation comprises the step of treating the slurry with phosphoric acid to control the pH values of the reaction mixture to within 5.0 to 7.0, the heat treatment temperature should preferably be 500° C.

Heat treatment can also be carried out using steam mixed with an inert gas such as nitrogen, argon, etc., and with air (when phosphoric acid is added to the steam).

Steam is fed in at a space velocity of 1.0 to 2.0 $h^{-1}$.

The feed rate of phosphoric acid used for catalyst heat treatment is 0.05 to 0.25 g/h per kg of catalyst.

Heat treatment times are within 2 to 50 hours, preferably between 20 and 30 hours. Space velocity for the organic compounds used is 0.7 to 1.5 $h^{-1}$, preferably 1.0 $h^{-1}$.

After the catalyst has been treated wih steam mixed with any one of the above-listed organic compounds or with steam mixed with an inert gas and any one of the above compounds in order to burn out the coke deposited on the catalyst surface, the catalyst is now subjected to regeneration by a mixture of steam and air at temperatures between 450° and 600° C., preferably between 500° and 550° C. Space velocity for air ranges from 500 to 700 $h^{-1}$, and for steam, from 1.0 to 2.0 $h^{-1}$.

The calcium phosphate catalyst thus obtained has the following characteristics: DMD conversion at the level of 96 to 97%, selectivity 86.0 to 87.5 mole %, coke deposition below 1%.

The following typical examples will further illustrate certain aspects of the present invention, deliniating more clearly the features and advantages specific to it.

EXAMPLE 1

The starting reactants used for catalyst preparation are 1.78 l of a calcium chloride solution containing 101.892 g of salt per 1 l of the solution and 1.608 l of a diammonium phosphate solution containing 51.02 g of salt per 1 l of the solution. An ammonia solution with a concentration of 152.15 g/l is added to the diammonium phosphate solution on the basis of having 2.33 moles of ammonia per 1 mole of diammonium phosphate immediately prior to the reaction.

The calcium chloride and diammonium phosphate solutions are gradually poured into a vessel fitted with a stirrer. The pouring procedure continues for 2 hours, the resulting slurry being continuously stirred all the while. Reaction is carried out with the solutions introduced kept practically in a constant ratio to ensure a calcium salt to phosphoric acid salt molar ratio of 2.5:1 and the slurry having a pH value within 9.0±0.05. The resultant slurry is treated with 150 ml of phosphoric acid concentrated to 281.26 g/l in order to reduce the pH value to 5.75. The resulting precipitate is separated from the reaction medium by filtration, washed with distilled water to remove chlorine ions, shaped into granules, and dried at ca. 120° C. The raw calcium phosphate thus obtained is loaded, in an amount of 24 cm$^3$, into a reactor which has the form of a quartz tube measuring 20 to 26 mm in diameter. The reactor is placed into an electrically heated oven. Steam mixed with phosphoric acid added on the basis of 0.2 g/h acid per 1 kg of catalyst is passed through the catalyst at 400° C. for 30 hours.

The resulting catalyst is test run in a DMD decomposition reaction in an atmosphere of steam. The DMD decomposition process is carried out at atmospheric pressure and a mean temperature of 320° C. for the duration of 2 hours.

DMD is fed in at the rate of 24 cm$^3$/h, and water at 48 cm$^3$/h, which gives a DMD space velocity of 1.0 h$^{-1}$ and a DMD to steam dilution ratio of 1:2.

The contact cycle is followed up by a regeneration cycle which comprises burning out the coke deposited on the catalyst and is to be repeated after every two hours of catalyst operation.

The regeneration cycle is carried out at 425° C., using 48 cm$^3$/h of water and 16,800 cm$^3$/h of air. The catalyst is analyzed using gas-liquid chromatography techniques. The quantity of coke deposited is determined by a conventional method.

The catalyst test results are presented hereinunder in Table 1.

EXAMPLE 2

The procedure used to prepare the calcium phosphate catalyst is the same as described in Example 1.

Heat treatment of the raw calcium phosphate is performed as described in Example 1, at 500° C.

The resulting catalyst is test run as described in Example 1.

The catalyst test results are presented hereinunder in Table 1.

EXAMPLE 3

The procedure used to prepare the calcium phosphate catalyst is the same as described in Example 1. Heat treatment of the raw calcium phosphate is performed as described in Example 1, at 600° C.

The resulting catalyst is test run as described in Example 1.

The catalyst test results are presented hereinunder in Table 1.

EXAMPLE 4

The procedure used to prepare the calcium phosphate catalyst is the same as described in Example 1. Heat treatment of the raw calcium phosphate is carried out at 500° C., using steam mixed with phosphoric acid added on the basis of 0.2 g/h of phosphoric acid per 1 kg catalyst and with nitrogen taken in an amount of 4800 cm$^3$ per hour, a gas space velocity being 200 h$^{-1}$.

The resulting catalyst is test run as described in Example 1.

The catalyst test results are presented hereinunder in Table 1.

EXAMPLE 5

The procedure used to prepare the calcium phosphate catalyst is the same as described in Example 1. Heat treatment of the raw calcium phosphate is carried out at 500° C., using steam mixed with phosphoric acid added on the basis of 0.2 g/h phosphoric acid per 1 kg catalyst and with air taken in an amount of 4800 cm$^3$/h, the space velocity of air being 200 h$^{-1}$.

The resulting catalyst is test run as descrined in Example 1.

The catalyst test results are presented hereinunder in Table 1.

EXAMPLE 6

The procedure used to prepare the calcium phosphate catalyst is the same as described in Example 1. Heat treatment of the raw calcium phosphate is carried out at 450° C., using steam with an addition of 7% by weight of aqueous solution of formaldehyde for the duration of 4 hours.

Steam space velocity (accounting for the 7% addition of the aqueous solution of formaldehyde) is 2.0 h$^{-1}$.

The resultant catalyst is subjected, prior to the test run, to a procedure for burning out the coke deposited on its surface, said procedure being carried out at 500° C., using 48 cm$^3$/h of water and 16,800 cm$^3$/h of air.

The catalyst thus prepared is test run as described in Example 1.

The catalyst test results are presented hereinunder in Table 1.

EXAMPLE 7

The procedure used to prepare the calcium phosphate catalyst is the same as described in Example 1.

Heat treatment of the raw calcium phosphate is performed as described in Example 6, at 500° C.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 8

The procedure used to prepare the calcium phosphate catalyst is the same as described in Example 1.

Heat treatment of the raw calcium phosphate is performed as described in Example 6, at 600° C.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 9

The procedure used to prepare the calcium phosphate catalyst is the same as described in Example 1.

Heat treatment of the raw calcium phosphate is carried out at 500° C., using steam with an addition of 5% by weight of acetaldehyde.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 10

The procedure used to prepare the calcium phosphate catalyst is the same as described in Example 1.

Heat treatment of the raw calcium phosphate is carried out at 400° C., using steam mixed with 7% by weight of aqueous solution of formaldehyde and with nitrogen in an amount of 4800 cm$^3$/h, the total corresponding to a gas space velocity 200 h$^{-1}$ and the heat treatment procedure continuing for 4 hours.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 11

The procedure used to prepare the calcium phosphate catalyst is the same as described in Example 1.

Heat treatment of the raw calcium phosphate is carried out at 500° C., using steam with an addition of 31.4% by weight of MDHP, for the duration of 2 hours. MDHP space velocity is 1.0 h$^{-1}$, steam space velocity, 2.0 h$^{-1}$.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 12

The procedure used to prepare the calcium phosphate catalyst is the same as described in Example 1.

Heat treatment of the raw calcium phosphate is carried out at 500° C., using steam with an addition of 31.6% by weight of MTHP, for the duration of 2 hours. MTHP space velocity us 1.0 h$^{-1}$, steam space velocity, 2.0 h$^{-1}$. The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 13

The procedure used to prepare the calcium phosphate catalyst is the same as described in Example 1.

Heat treatment of the raw calcium phosphate and the coke deposit burning-out procedure that follows are carried out as described in Example 11, at 400° C.

The resultant catalyst is test run as described in Example 1.

The catalyst test results are presented hereinunder in Table 1.

EXAMPLE 14

The procedure used to prepare the calcium phosphate catalyst is the same as described in Example 1.

Heat treatment of the raw calcium phosphate and the coke deposit burning-out procedure that follows are carried out as described in Example 11, at 600° C.

The catalyst so prepared is test run as described in Example 1.

The catalyst test results are presented hereinunder in Table 1.

EXAMPLE 15

The procedure used to prepare the calcium phosphate catalyst is the same as described in Example 1.

Heat treatment of the raw calcium phosphate is carried out at 500° C. for 2 hours, using steam mixed with 31.4% by weight of MDHP and with nitrogen in an amount of 4800 cm$^3$ per hour, the total corresponding to a gas space velocity of 200 h$^{-1}$.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 16

The procedure used to prepare the calcium phosphate catalyst is the same as described in Example 1.

Heat treatment of the raw calcium phosphate is carried out at 500° C. for the duration of 2 hours, using steam mixed with 28.3% by weight of trimethyl carbinol (TMC). TMC space velocity is 1.0 h$^{-1}$, that of steam, 2.0 h$^{-1}$ (on the liquid basis).

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 17

The procedure used to prepare the calcium phosphate catalyst is the same as described in Example 1.

Heat treatment of the raw calcium phosphate is carried out at 500° C. for the duration of 2 hours, using steam mixed with 30.9% by weight of isopropenyl ethyl carbinol (IPEC). IPEC space velocity is 1.0 h$^{-1}$, that of steam, 2.0 h$^{-1}$ (on the liquid basis).

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 18

The procedure used to prepare the calcium phosphate catalyst is the same as described in Example 1.

Heat treatment of the raw calcium phosphate and the coke deposit burning-out procedure that follows are carried out as described above in Example 16, at 400° C.

The resultant catalyst is test run as described in Example 1.

The catalyst test results are presented hereinunder in Table 1.

EXAMPLE 19

The procedure used to prepare the calcium phosphate catalyst is the same as described in Example 1.

Heat treatment of the raw calcium phosphate and the coke deposit burning-out procedure that follows are carried out as described above in Example 16, at 600° C.

The resultant catalyst is test run as described in Example 1.

The catalyst test results are presented hereinunder in Table 1.

EXAMPLE 20

The procedure used to prepare the calcium phosphate catalyst is the same as described in Example 1.

Heat treatment of the raw calcium phosphate is carried out at 500° C. for the duration of 6 hours, using steam mixed with 28.3% by weight TMC and that of nitrogen in an amount of 4800 cm$^3$ per hour, the total corresponding to a gas space velocity of 200 h$^{-1}$.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 21

The procedure used to prepare the calcium phosphate catalyst is the same as described in Example 1.

Heat treatment of the raw calcium phosphate is carried out at 450° C. during 9 hours, using steam with an addition of 25.4% by weight of isoprene. Isoprene space velocity is 1.0 h$^{-1}$, that of steam, 2.0 h$^{-1}$ (on the liquid basis).

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 22

The procedure used to prepare the calcium phosphate catalyst is the same as described in Example 1.

Heat treatment of the raw calcium phosphate and the coke deposit burning-out procedure that follows are carried out as described above in Example 21, at 500° C.

The catalyst so prepared is test run as described in Example 1.

The catalyst test results are presented hereinunder in Table 1.

EXAMPLE 23

The procedure used to prepare the calcium phosphate catalyst is the same as described in Example 1.

Heat treatment of the raw calcium phosphate and the coke deposit burning-out procedure that follows are carried out as described above in Example 21, at 600° C.

The catalyst so prepared is test run as described in Example 1.

The catalyst test results are presented hereinunder in Table 1.

EXAMPLE 24

The procedure used to prepare the calcium phsophate catalyst is the same as described in Example 1.

Heat treatment of the raw calcium phosphate is carried out at 500° C. during 9 hours, using steam mixed with 25.4% by weight of isoprene and with nitrogen taken in an amount of 4800 cm$^3$ per hour, the total corresponding to gas space velocity of 200 h$^{-1}$.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 25

The procedure used to prepare the calcium phosphate catalyst is the same as described in Example 1.

Heat treatment of the raw calcium phosphate is carried out at 500° C. for the duration of 9 hours, using steam mixed with 25.3% by weight of piperylene. Piperylene space velocity is 1.0 h$^{-1}$, that of steam, 2.0 h$^{-1}$.

The resultant catalyst is subjected, prior to the test run, to the procedure for burning out the coke deposited on its surface as described above in Example 6.

The catalyst so prepared is test run as described in Example 1.

The catalyst test results are presented hereinunder in Table 1.

EXAMPLE 26

The starting reactants used for catalyst preparation are 1.18 l of a calcium chloride solution containing 99.8 g of calcium chloride in 1 l of solution and 2.0 l of a disodium phosphate solution containing 50.21 g of salt in 1 l of solution. An ammonia solution with a concentration of 130 g/l is added to the disodium phosphate solution on the basis of having 1.3 moles of ammonia per 1 mole of disodium phosphate immediately prior to the reaction.

The calcium chloride and disodium phosphate solutions are gradually poured into a vessel fitted with a stirrer. The pouring procedure continues for 2 hours, the resulting slurry being continuously stirred all the while. Reaction is carried out with the solutions introduced kept in a constant volume ratio to ensure a calcium chloride to disodium phosphate molar ratio of 1.5:1 and the slurry having a pH value of 9.0±0.05. The resulting precipitate is separated by filtration, washed with distilled water to remove chlorine ions, shaped into granules, and dried at a temperature of 120° C. Heat treatment of the raw calcium phosphate is performed as described in EXample 1, using a temperature of 500° C.

The catalyst so prepared is test run as described in Example 1, using a contact temperature of 375° C.

The catalyst test results are presented hereinunder in Table 1.

EXAMPLE 27

The procedure used to prepare the calcium phosphate catalyst is the same as described in Example 26.

Heat treatment of the raw calcium phosphate is carried out as described in Example 1, using a temperature of 400° C.

The catalyst so prepared is test run as described in Example 26.

The catalyst test results are presented hereinunder in Table 1.

EXAMPLE 28

The procedure used to prepare the calcium phosphate catalyst is the same as described in Example 26.

Heat treatment of the raw calcium phosphate is performed as described in Example 6. The resultant catalyst is subjected, prior to the test run, to the procedure for burning out the coke deposited on its surface as described above in Example 6.

The catalyst so prepared is test run as described in Example 26.

The catalyst test results are presented hereinunder in Table 1.

EXAMPLE 29

The procedure used to prepare the calcium phosphate catalyst is the same as described in Example 26.

Heat treatment of the raw calcium phosphate is carried out as described in Example 13. The resultant catalyst is subjected, prior to the test run, to the procedure for burning out the coke deposited on its surface as described above in Example 6.

The catalyst so prepared is test run as described in Example 26.

The catalyst test results are presented hereinunder in Table 1.

In describing the above examples of embodiments of the present invention, a limited terminology has been employed for greater clarity. it will be understood, however, that the present invention is by no means limited by the terminology adopted herein and that each of the terms used covers all equivalent elements such as may serve the same function and be used to solve the same problems.

Although the present invention has been described herein with reference to the preferred typical embodiments thereof, it will be apparent to those skilled in the art that there may be minor modifications made in the procedures comprised in the inventive method of calcium phosphate catalyst preparation without departing from the spirit of the invention.

All such modifications and variations are contemplated to be embraced in the spirit and scope of the invention, as defined in the appended claims.

TABLE 1

RESULTS OF CATALYST TESTING IN DMD DECOMPOSITION RUNS

Operating temperature: 320° C.
DMD volume flow rate: 1 h$^{-1}$
DMD: H$_2$O dilution ratio: 1:2

| Catalysts as per Example Nos. | Characteristic values | | |
|---|---|---|---|
| | DMD conversion, % | Selectivity, mole % | Coke formation, mole % |
| 1 | 2 | 3 | 4 |
| 1 | 97.5 | 86.9 | 1.53 |
| 2 | 97.2 | 87.2 | 0.84 |
| 3 | 96.0 | 87.5 | 0.56 |
| 4 | 97.4 | 86.9 | 1.04 |
| 5 | 97.3 | 86.8 | 1.09 |
| 6 | 97.5 | 87.0 | 1.50 |
| 7 | 97.3 | 87.5 | 0.54 |
| 8 | 96.0 | 87.3 | 0.47 |
| 9 | 97.4 | 87.3 | 0.61 |
| 10 | 97.4 | 86.9 | 1.58 |
| 11 | 97.2 | 87.3 | 0.65 |
| 12 | 97.2 | 87.2 | 0.69 |
| 13 | 97.4 | 86.9 | 1.60 |
| 14 | 95.9 | 87.5 | 0.48 |
| 15 | 97.3 | 87.2 | 0.80 |
| 16 | 97.1 | 87.0 | 0.70 |
| 17 | 97.0 | 87.2 | 0.68 |
| 18 | 97.5 | 86.8 | 1.70 |
| 19 | 95.8 | 87.4 | 0.46 |
| 20 | 97.1 | 86.9 | 0.74 |
| 21 | 97.4 | 86.9 | 1.61 |
| 22 | 96.8 | 87.1 | 0.63 |
| 23 | 95.9 | 87.5 | 0.56 |
| 24 | 97.0 | 87.0 | 0.72 |
| 25 | 96.9 | 87.3 | 0.66 |
| 26 | 94.7 | 87.2 | 0.59 |
| 27 | 95.2 | 86.4 | 1.78 |
| 28 | 95.0 | 86.6 | 0.52 |
| 29 | 94.8 | 87.0 | 0.50 |
| 30 | 94.7 | 86.8 | 0.52 |
| 31 | 94.9 | 86.6 | 0.58 |

What is claimed is:

1. A method of preparing a calcium phosphate catalyst, comprising reacting a water-soluble calcium salt with a water-soluble phosphoric acid salt in aqueous ammonia to form a precipitate, separating said precipitate from the reaction mixture, shaping said precipitate, drying said precipitate, and subjecting said precipitate to heat treatment within a temperature range of 450° to 600° C. in the presence of steam mixed with phosphoric acid, or an organic compound, or phosphoric acid and an inert gas, or phosphoric acid and air, or an organic compound and an inert gas, said organic compound being selected from the group consisting of an aldehyde, an oxygen-containing heterocyclic compound, an alcohol, and a diene hydrocarbon.

2. A method according to claim 1, wherein the molar ratio of said calcium salt to said phosphoric acid salt in said aqueous ammonia is within the range of 1.5:1 to 5.0:1, and the reaction mixture obtained is treated with a solution of phosphoric acid to a pH of from 5.0 to 7.0.

3. A method according to claim 2, wherein the reaction mixture is treated with a solution of phosphoric acid to a pH of from 5.5 to 6.0.

4. A method according to claim 1, wherein said aldehyde is acetaldehyde.

5. A method according to claim 1, wherein said oxygen-containing heterocyclic compound is methyl dihydropyrane.

6. A method according to claim 1, wherein said oxygen-containing heterocyclic compound is methylene tetrahydropyrane.

7. A method according to claim 1, wherein said alcohol is trimethyl carbinol.

8. A method according to claim 1, wherein said alcohol is isopropenyl ethyl carbinol.

9. A method according to claim 1, wherein said diene hydrocarbon is isoprene.

10. A method according to claim 1, wherein said diene hydrocarbon is piperylene.

11. A method according to claim 1, wherein the molar ratio of said calcium salt to said phosphoric acid salt in said aqueous ammonia is 1.5:1.